US011154626B2

(12) United States Patent
Kamiko et al.

(10) Patent No.: US 11,154,626 B2
(45) Date of Patent: Oct. 26, 2021

(54) EVALUATION METHOD AND EVALUATION DEVICE

(71) Applicants: Nikkiso Co., Ltd., Tokyo (JP); THE RITSUMEIKAN TRUST, Kyoto (JP)

(72) Inventors: Naoyuki Kamiko, Kusatsu (JP); Shotaro Hashimoto, Kusatsu (JP); Hiroaki Mochizuki, Tokyo (JP)

(73) Assignees: NIKKISO CO., LTD., Tokyo (JP); THE RITSUMEIKAN TRUST, Kyoto (JP)

( * ) Notice: Subject to any disclaimer, the term of this patent is extended or adjusted under 35 U.S.C. 154(b) by 248 days.

(21) Appl. No.: 16/293,209

(22) Filed: Mar. 5, 2019

(65) Prior Publication Data

US 2019/0275183 A1 Sep. 12, 2019

(30) Foreign Application Priority Data

Mar. 9, 2018 (JP) ............................ JP2018-043555

(51) Int. Cl.
*A61L 2/28* (2006.01)
*A61L 2/00* (2006.01)
*A61L 2/10* (2006.01)

(52) U.S. Cl.
CPC ............... *A61L 2/0029* (2013.01); *A61L 2/10* (2013.01); *A61L 2/28* (2013.01)

(58) Field of Classification Search
CPC .... A61L 2/0029; A61L 2/0035; A61L 2/0041; A61L 2/0047; A61L 2/0052;

(Continued)

(56) References Cited

U.S. PATENT DOCUMENTS 8,828,714 B2 * 9/2014 Nishikawa ................ A61L 9/18 435/287.4

FOREIGN PATENT DOCUMENTS

JP 2004159508 A 6/2004

OTHER PUBLICATIONS

Ryan et al.,"Inactivation of Airborne Microorganisms Using Novel Ultraviolet Radiation Sources in Reflective Flow-Through Control Devices," Aerosol Science and Technology, 44:541-550, 2010 (Year: 2010).*

(Continued)

*Primary Examiner* — Timothy C Cleveland

(74) *Attorney, Agent, or Firm* — Muncy, Geissler, Olds & Lowe, P.C.

(57) ABSTRACT

An evaluation device includes: a processing container that has an intake port and an exhaust port; a microorganism supply device that floats microorganisms in the air inside the processing container; a light source that irradiates the microorganisms floating in the air inside the processing container with ultraviolet rays while the intake port and the exhaust port are in a state of being closed; and a microorganism recovery device that is connected to the exhaust port. The microorganism recovery device discharges air that has a volume larger than the capacity of the inside of the processing container through the exhaust port while introducing air that does not contain microorganisms to be evaluated into the inside of the processing container through the intake port after the irradiation with the ultraviolet rays and recovers the microorganisms contained in the air that is discharged.

5 Claims, 4 Drawing Sheets

(58) Field of Classification Search
CPC ...... A61L 2/0058; A61L 2/0064; A61L 2/007; A61L 2/0076; A61L 2/08; A61L 2/081; A61L 2/082; A61L 2/084; A61L 2/085; A61L 2/087; A61L 2/088; A61L 2/10; A61L 2/12; A61L 2/28
See application file for complete search history.

(56) References Cited

OTHER PUBLICATIONS

Office Action issued in corresponding JP patent application No. 2018-043555 dated Apr. 7, 2020 (with English translation).

* cited by examiner

EVALUATION METHOD AND EVALUATION DEVICE

RELATED APPLICATION

Priority is claimed to Japanese Patent Application No. 2018-043555, filed on Mar. 9, 2018, the entire content of which is incorporated herein by reference.

BACKGROUND OF THE INVENTION

1. Field of the Invention

The present invention relates to an evaluation method and an evaluation device for evaluating inactivation performance of microorganisms floating in a space.

2. Description of the Related Art

It is known that ultraviolet rays have sterilization capability, and ultraviolet ray irradiation devices are used for sterilization treatment in medical and food processing scenes, and the like. In the sterilization treatment with ultraviolet rays, sterilization performance is evaluated on the illuminance of ultraviolet rays irradiating an object to be treated, that is, the amount of energy incident on a unit area. A technique of performing sterilization treatment on floating microorganisms in the air using positive ions and negative ions generated by an ionization phenomenon such as discharge is also known. In devices for the latter case, sterilization performance is evaluated on the ion concentration in the air.

In the technique described in Patent Document 1, since a part of the air in a space where sterilization treatment has been performed is collected and evaluated, it is difficult to accurately understand how effectively the energy used for the sterilization treatment has worked. Performance for inactivating microorganisms floating in the space can be preferably measured quantitatively by irradiating the space with ultraviolet rays.

SUMMARY OF THE INVENTION

In this background, a purpose of the present invention is to provide a technique for evaluating inactivation performance of microorganisms floating in a space.

An evaluation method according to one embodiment of the present invention includes: floating microorganisms in the air inside a processing container having an intake port and an exhaust port; irradiating the microorganisms floating in the air inside the processing container with ultraviolet rays while the intake port and the exhaust port are in a state of being closed; discharging air that has a volume larger than the capacity of the inside of the processing container through the exhaust port while introducing air that does not contain microorganisms to be evaluated into the inside of the processing container through the intake port after the irradiation with the ultraviolet rays so as to recover the microorganisms contained in the air that is discharged; measuring the amount of the microorganisms that have been recovered; and evaluating the inactivation amount of the microorganisms with respect to the average integrated illuminance of the ultraviolet rays inside the processing container in the irradiating.

According to this embodiment, by discharging air having a volume larger than the capacity of the inside of the processing container after the irradiation with ultraviolet rays so as to recover microorganisms, microorganisms remaining inside the processing container after the irradiation with ultraviolet rays can be recovered without fail. Thereby, the accuracy of quantitative evaluation of the inactivation amount of the microorganisms can be improved.

In the irradiating, the inside of the processing container may be irradiated with ultraviolet rays while stirring the air inside the processing container.

In the floating of the microorganisms, air that has a volume larger than the capacity of the inside of the processing container and that contains the microorganisms may be introduced through the intake port while discharging the air inside the processing container through the exhaust port.

In the floating of the microorganisms, microorganisms put inside the processing container may be dispersed in the air inside the processing container.

The average integrated illuminance of the ultraviolet rays may be calculated by multiplying average illuminance, which is the average value of the respective illuminances of the ultraviolet rays on a plurality of virtual planes set inside the processing container, by irradiation time of the ultraviolet rays.

The plurality of virtual planes may be set so as to be orthogonal to a predetermined irradiation direction of the ultraviolet rays.

Another embodiment of the present invention relates to an evaluation device. This device includes: a processing container that has an intake port and an exhaust port; a microorganism supply device that floats microorganisms in the air inside the processing container; a light source that irradiates the microorganisms floating in the air inside the processing container with ultraviolet rays while the intake port and the exhaust port are in a state of being closed; and a microorganism recovery device that is connected to the exhaust port. The microorganism recovery device discharges air that has a volume larger than the capacity of the inside of the processing container through the exhaust port while introducing air that does not contain microorganisms to be evaluated into the inside of the processing container through the intake port after the irradiation with the ultraviolet rays and recovers the microorganisms contained in the air that is discharged.

According to this embodiment, by discharging air having a volume larger than the capacity of the inside of the processing container after the irradiation with ultraviolet rays so as to recover microorganisms, microorganisms remaining inside the processing container after the irradiation with ultraviolet rays can be recovered without fail. Thereby, the accuracy of quantitative evaluation of the inactivation amount of the microorganisms can be improved.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Hereinafter, an embodiment for carrying out the present invention will be described in detail with reference to the accompanying drawing. Like numerals are used in the description to denote like elements and the description may be omitted as appropriate.

Figure 1:
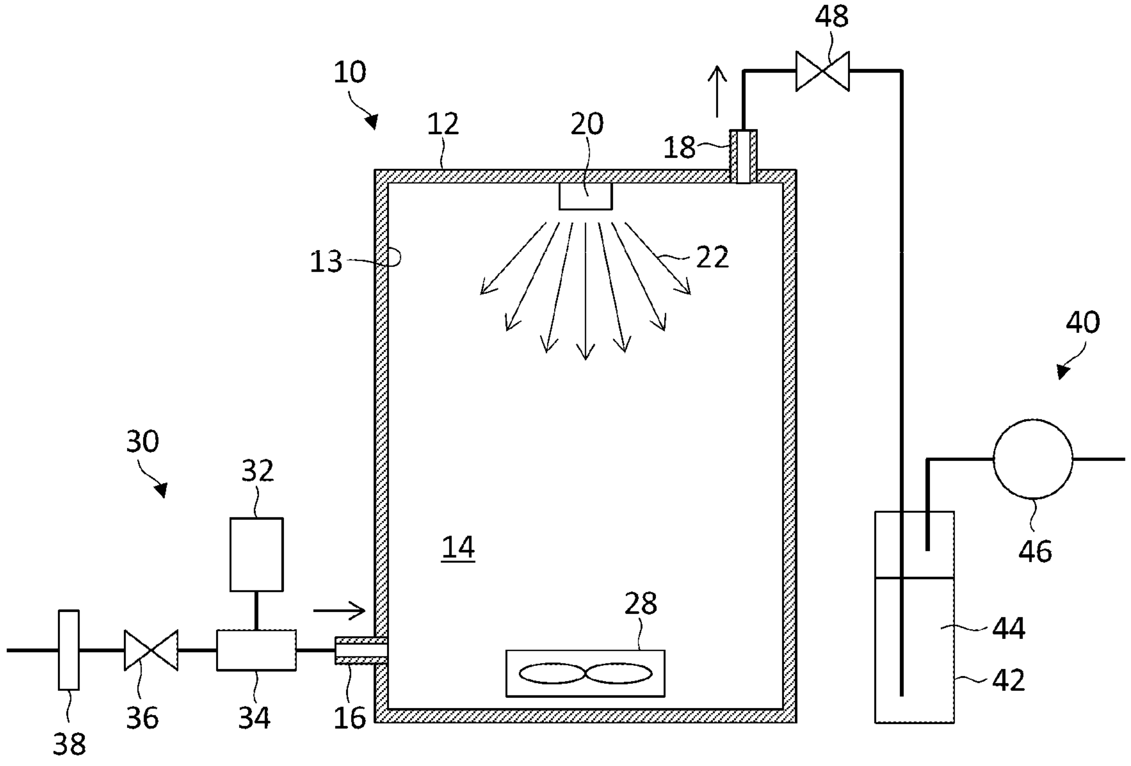
FIG. 1 is a diagram schematically showing the configuration of an evaluation device according to an embodiment.

FIG. 1 is a diagram schematically showing the configuration of an evaluation device 10 according to an embodiment. The evaluation device 10 includes a processing container 12, a light source 20, a microorganism supply device 30, and a microorganism recovery device 40. The evaluation device 10 is used to irradiate microorganisms floating in the air in an internal space 14 of the processing container 12 with ultraviolet rays 22 from the light source 20 and to measure and evaluate the inactivation performance (for example, death rate) of the microorganisms by the ultraviolet irradiation. Examples of microorganisms to be tested include bacteria such as Escherichia coli and Bacillus subtilis, fungi such as molds, protozoa, and the like.

The processing container 12 surrounds the internal space 14 where an ultraviolet irradiation process is performed. The shape of the processing container 12 is not limited and may be, for example, a cylindrical shape, a rectangular parallelepiped shape, or the like. The material of the processing container 12 is not particularly limited; however, at least the inner surface 13 of the processing container 12 is preferably made of a material having ultraviolet resistance. The inner surface 13 of the processing container 12 can be made of, for example, a fluorine-based resin such as polytetrafluoroethylene (PTFE) or a metal material such as stainless steel.

The processing container 12 has an intake port 16 and an exhaust port 18. The intake port 16 is connected to the microorganism supply device 30, and air containing microorganisms to be tested is introduced. The exhaust port 18 is connected to the microorganism recovery device 40, and air after the ultraviolet irradiation is discharged.

The light source 20 is arranged so as to output ultraviolet rays 22 toward the internal space 14 of the processing container 12. In the illustrated example, the light source 20 is provided in the internal space 14 of the processing container 12 and attached to the inner surface 13 of the processing container 12. The light source 20 may be provided outside the processing container 12 or may irradiate the internal space 14 of the processing container 12 with ultraviolet rays via a window member provided on a part of the wall of the processing container 12. The window member can be made of a glass material such as quartz ($SiO_2$), sapphire ($Al_2O_3$), or an amorphous fluorine-based resin.

The light source 20 includes, for example, an LED (Light Emitting Diode) that outputs ultraviolet rays 22. The LED of the light source 20 preferably have a center wavelength or peak wavelength of light emission in a range of about 200 nm to 350 nm and emit ultraviolet rays of around 260 nm to 290 nm, which is a range for a high disinfection efficiency wavelength. As such an ultraviolet ray LED, for example, those in which aluminum gallium nitride (AlGaN) is used are known. The light source 20 may be of a type different from LEDs such as so-called sterilizing lamps and ultraviolet lamps.

In the processing container 12, a stirring device 28 is provided. The stirring device 28 stirs the air in the internal space 14 of the light source 20 so as to allow the microorganisms to float such that the entire air in the internal space 14 is uniformly irradiated with ultraviolet rays 22. The stirring device 28 can be constituted by, for example, a blower fan.

The microorganism supply device 30 includes a spraying unit 32, a mixing unit 34, an intake valve 36, and an intake filter 38. The spraying unit 32 sprays the microorganisms to be tested and mixes the microorganisms into the air. The mixing unit 34 mixes the air flowing toward the intake port 16 and the microorganisms supplied from the spraying unit 32. The air flowing toward the intake port 16 is supplied through the intake filter 38 and the intake valve 36. The intake filter 38 is a sterilizing filter capable of removing microorganisms and is formed using, for example, an HEPA (High Efficiency Particulate Air) filter or the like.

The microorganism supply device 30 supplies the air including the microorganisms to the intake port 16 by operating the spraying unit 32 in a state where the intake valve 36 is open. The microorganism supply device 30 may adjust the number or concentration of microorganisms supplied to the intake port 16 by controlling the operation of the spraying unit 32. The microorganism supply device 30 supplies clean air containing no microorganism to the intake port 16 by leaving the intake valve 36 in a state of being open without operating the spraying unit 32.

The microorganism recovery device 40 includes an impinger 42, an exhaust pump 46, and an exhaust valve 48. The impinger 42 is an instrument for recovering microorganisms by a so-called liquid collection method. The air containing microorganisms discharged from the exhaust port 18 passes through a collection liquid 44 of the impinger 42, and the air is thereby discharged to the outside of the impinger 42 while the microorganisms stay in the collection liquid 44. By operating the exhaust pump 46 while the exhaust valve 48 is open, the air from the exhaust port 18 passes through the collection liquid 44 of the impinger 42, and the microorganisms are recovered in the collection liquid 44. The microorganism recovery device 40 may recover the microorganisms by a so-called filtration collection method. For example, the air containing the microorganisms may pass through a filter such that the microorganisms stay at the filter.

The amount of the microorganisms recovered by the microorganism recovery device 40 is measured using a publicly-known technique. For example, there are a method of measuring the biological activity of the microorganisms contained in the collection liquid 44, a method of measuring the remaining amount of the microorganisms by culturing the microorganisms contained in the collection liquid 44 and counting the number of colonies, and the like.

Next, the concept of ultraviolet illuminance in the internal space 14 of the processing container 12 will be described. In general, when sterilization treatment is performed by irradiating a target with ultraviolet rays, the sterilization performance is often evaluated based on the illuminance ($W/cm^2$) of ultraviolet rays on the irradiated surface. However, when irradiating a space with ultraviolet rays as in the present embodiment, it is difficult to set a single "irradiated surface". Therefore, in the present embodiment, a plurality of virtual planes is set in the internal space 14, and the sterilization performance is evaluated based on the "average illuminance" obtained by averaging the illuminance on each virtual plane.

Figure 2:
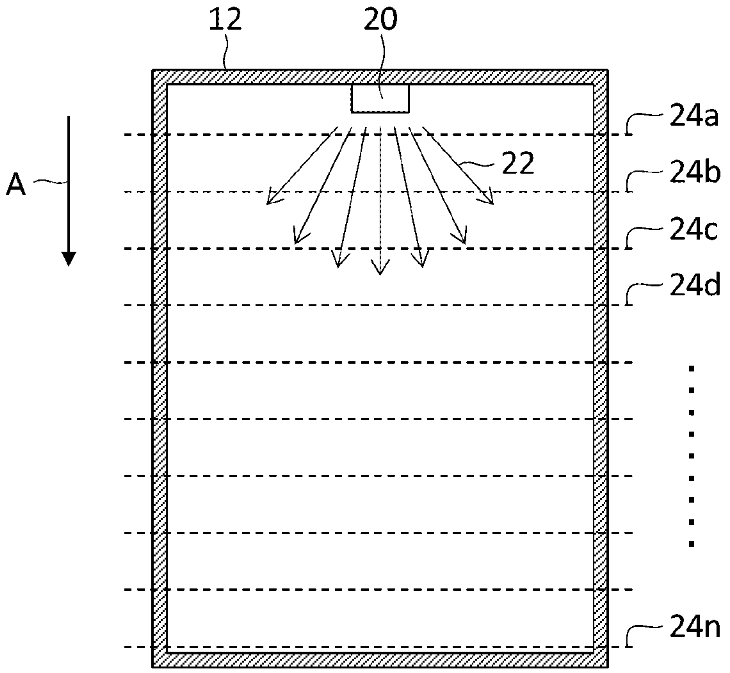
FIG. 2 is a diagram schematically showing a plurality of virtual planes set in an internal space of a processing container in order to calculate average illuminance.

FIG. 2 is a diagram schematically showing a plurality of virtual planes 24*a* to 24*n* set in the internal space 14 of the processing container 12 in order to calculate the average illuminance. The plurality of virtual planes 24*a* to 24*n* (collectively, also referred to as virtual plane 24) are set so as to be orthogonal to a specific irradiation direction A of the ultraviolet rays 22 and are set to be arranged at equal intervals in the specific irradiation direction A.

Figure 3:
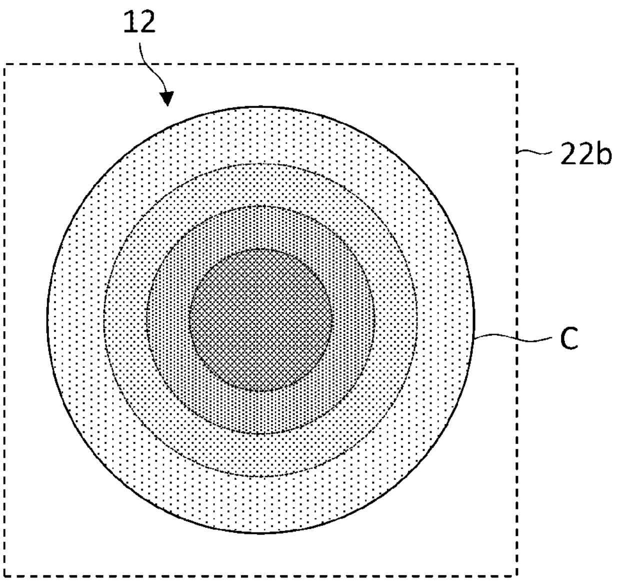
FIG. 3 is a diagram schematically showing an example of illuminance distribution on a virtual plane.

FIG. 3 is a diagram schematically showing an example of illuminance distribution on the virtual plane 24*b* and shows illuminance distribution in a region C corresponding to the internal space 14 of the processing container 12. In the example shown in FIG. 3, a distribution is shown where the illuminance in the vicinity of the center of the region C is high and the illuminance decreases as the distance from the center increases. By dividing, by the area S ($cm^2$) of the region C, the total value P(W) of the intensity of the ultraviolet rays 22 incident on one virtual plane 24*b* thus set, the illuminance $E(W/cm^2)=P/S$ is obtained.

Further, by averaging illuminances Ea to En calculated respectively at the plurality of virtual planes 24*a* to 24*n* as shown in FIG. 2, an average illuminance Eav of the entire internal space 14 of the processing container 12 can be obtained. By multiplying the calculated average illuminance Eav by irradiation time t of the ultraviolet rays 22, an average integrated illuminance $D(J/cm^2)=Eav*t$ of the ultraviolet rays acting on the internal space 14 can be obtained.

The average illuminance Eav of the processing container 12 may be calculated based on the measurement result of the illuminance of the ultraviolet rays 22 using the actual processing container 12 or may be calculated based on the result of optical simulation. In the former case, the average illuminance Eav can be obtained by actually measuring the illuminances at a plurality of virtual planes while changing the distance from the light source 20. In the latter case, after creating an optical model simulating the processing container 12, the average illuminance Eav can be obtained by calculating the illuminances at a plurality of virtual planes by executing a simulation such as ray tracing on the optical model.

Next, an evaluation procedure using the evaluation device 10 will be described. First, air containing microorganisms of a predetermined concentration is introduced into the internal space 14 of the processing container 12. The exhaust pump 46 is operated while the intake valve 36 and the exhaust valve 48 are in a state of being open such that the air flows into the processing container 12. By operating the spraying unit 32 in this state, the air containing the microorganisms of the predetermined concentration fills the internal space 14 of the processing container 12. At this time, air containing microorganisms whose volume is larger than the capacity of the internal space 14 is preferably introduced into the processing container 12. By introducing the air containing microorganisms that exceeds the capacity of the internal space 14, it is ensured that the concentration of the microorganisms in the internal space 14 reaches the predetermined concentration, and the evaluation accuracy can be improved.

Next, the intake valve 36 and the exhaust valve 48 are closed such that the internal space 14 is hermetically sealed. The light source 20 is turned on in the sealed state to irradiate the internal space 14 with the ultraviolet rays 22, and the stirring device 28 is operated so that the air in the internal space 14 is stirred. After a predetermined irradiation time has elapsed, the light source 20 is turned off, and the operation of the stirring device 28 is stopped. Further, during the irradiation process of the ultraviolet rays 22, the collection liquid 44 of the microorganism recovery device 40 is replaced so that the collection liquid 44 does not contain any microorganisms.

Next, the intake valve 36 and the exhaust valve 48 are opened, and the exhaust pump 46 is operated such that the air in the internal space 14 irradiated with ultraviolet rays is discharged and microorganisms contained in the discharged air are recovered in the collection liquid 44. At this time, air having a volume that is larger than the capacity of the internal space 14 is preferably discharged, and air in the internal space 14 is preferably collected while introducing air that does not contain microorganisms to be evaluated into the processing container 12 through the intake valve 36. By discharging air exceeding the capacity of the internal space 14, most of the microorganisms remaining in the internal space 14 can be recovered by the microorganism recovery device 40, and the evaluation accuracy can be improved.

Next, the amount of the microorganisms recovered by the microorganism recovery device 40 is measured, and the number of surviving microorganisms is obtained. The residual concentration of the microorganisms remaining in the internal space 14 after the irradiation with the ultraviolet rays is obtained by dividing the obtained number of surviving microorganisms by the capacity of the internal space 14. Further, by calculating the average integrated illuminance D based on the average illuminance Eav of the ultraviolet rays 22 and the irradiation time t, the inactivation performance of the microorganisms with respect to the average integrated illuminance D can be evaluated.

A control test may be performed so as to obtain the residual concentration of the microorganisms in the case of no irradiation with the ultraviolet rays 22. More specifically, a step of introducing air containing the microorganisms into the internal space 14, a step of stirring the internal air for a predetermined period of time while keeping the internal space 14 in a sealed state, a step of discharging the air after the stirring so as to recover the remaining microorganisms, and a step of measuring the amount of microorganisms that have been recovered are performed. At this time, by having the same test conditions except for having no irradiation with the ultraviolet rays 22 in the step of stirring, the residual concentration of the microorganisms in the case of no irradiation with the ultraviolet rays 22 is obtained. After that, the residual concentration (the concentration at the time of irradiation) of the microorganisms when irradiation with the ultraviolet rays 22 is performed is divided by the residual concentration (the concentration at the time of no irradiation) of the microorganisms when irradiation with the ultraviolet rays 22 is not performed so as to obtain the inactivation rate (=the concentration at the time of irradiation/the concentration at the time of no irradiation). By comparing this inactivation rate with the average integrated illuminance D, the inactivation performance of the microorganisms may be evaluated.

Furthermore, by obtaining the inactivation rate of the microorganisms by changing the irradiation intensity and the irradiation time of the ultraviolet rays 22, the tendency of the change of the inactivation rate when the average integrated illuminance D of the ultraviolet rays 22 is changed can be obtained. Thereby, the inactivation performance of the microorganisms with respect to the average integrated illuminance D can be evaluated more suitably.

Figure 4:
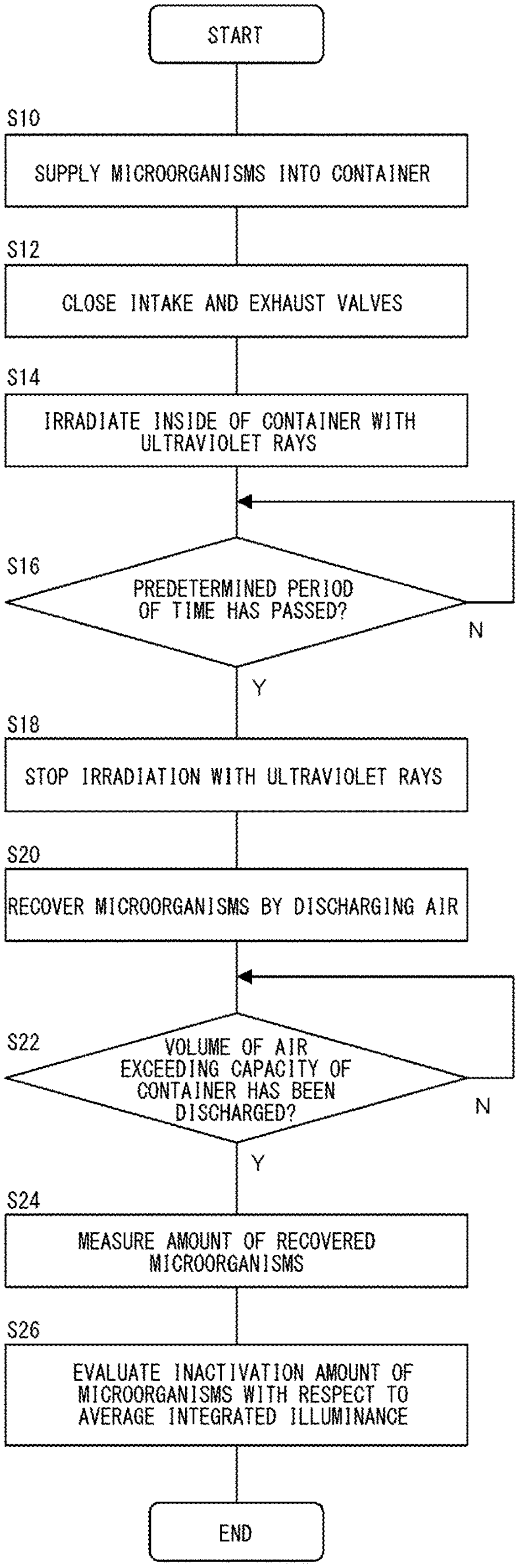
FIG. 4 is a flowchart showing a flow of an evaluation method according to an embodiment.

FIG. 4 is a flowchart showing a flow of an evaluation method according to the embodiment. First, microorganisms are supplied into the processing container 12 (S10), and the intake valve 36 and the exhaust valve 48 are closed to bring the processing container 12 into a sealed state (S12). The internal space 14 of the processing container 12 is irradiated with the ultraviolet rays 22 from the light source 20 (S14), the irradiation with ultraviolet rays is continued until a predetermined period of time has passed (N of S16), and the irradiation with ultraviolet rays is stopped after the predetermined period of time has passed (S18). Subsequently, the intake valve 36 and the exhaust valve 48 are opened to discharge the air in the internal space 14 after the irradiation with ultraviolet rays (S20), the discharging is continued until the volume exceeds the capacity of the internal space 14 (N of S22), and when the volume exceeding the capacity of the internal space 14 has been discharged (Y in S22), the amount of microorganisms recovered by the microorganism recovery device 40 is measured (S24). Subsequently, the inactivation amount of the microorganisms is evaluated with respect to the average integrated illuminance D of the ultraviolet rays 22 (S26), and the present flow is ended.

According to the present embodiment, introduction of air containing microorganisms having a volume larger than the capacity of the internal space 14 of the processing container 12 allows the microorganism concentration in the internal space 14 before the irradiation with ultraviolet rays to be a predetermined concentration. By discharging air having a volume larger than the capacity of the internal space 14 of the processing container 12 after the irradiation with ultraviolet rays, most of the microorganisms remaining in the internal space 14 after the irradiation with ultraviolet rays can be recovered. Thereby, the accuracy of measuring the amount of microorganisms can be improved. Furthermore, by using the average illuminance in order to numerically evaluate the irradiation mode of the ultraviolet rays 22 in the internal space 14, the performance of the irradiation with ultraviolet rays on the space can be appropriately evaluated numerically.

Figure 5:
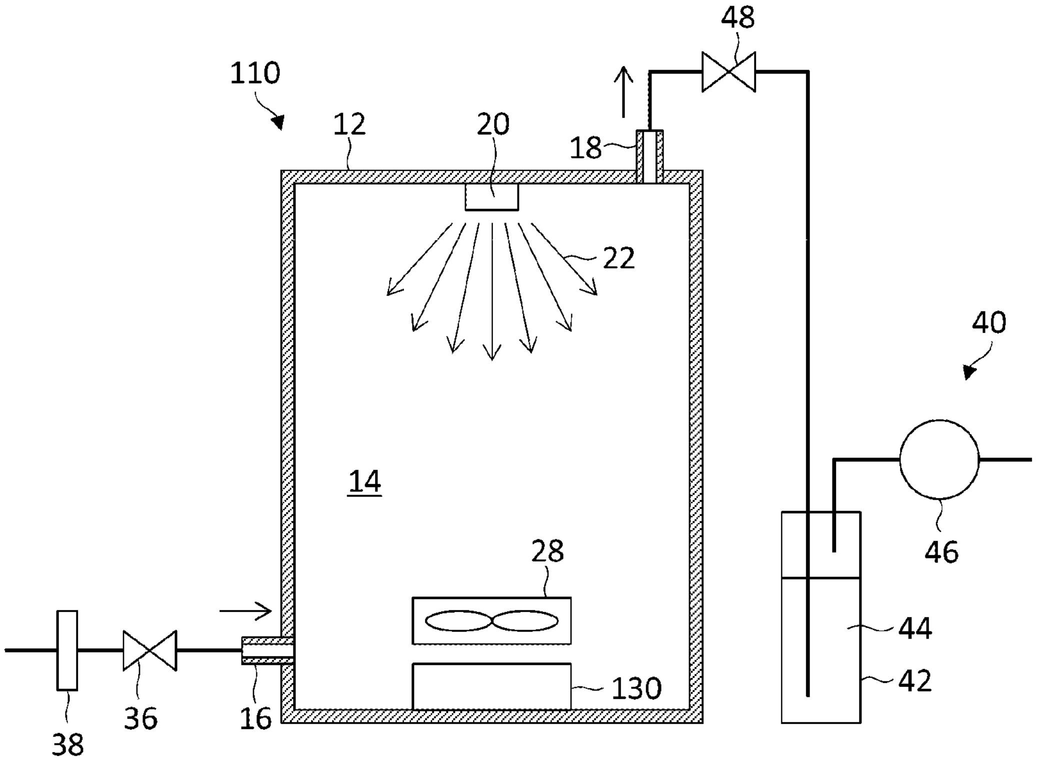
FIG. 5 is a diagram schematically showing the configuration of an evaluation device according to an exemplary variation.

FIG. 5 is a diagram schematically showing the configuration of an evaluation device 110 according to an exemplary variation. This exemplary variation is different from the above embodiment in that a microorganism supply device 130 is provided in the internal space 14 of the processing container 12. Hereinafter, the present exemplary variation will be described focusing on differences from the above-described embodiment, and descriptions of common features are omitted as appropriate.

The evaluation device 110 includes a processing container 12, a light source 20, a microorganism supply device 130, and a microorganism recovery device 40. The microorganism supply device 130 is arranged inside the processing container 12 and is configured so as to directly supply microorganisms to the internal space 14. The microorganism supply device 130, for example, holds powdered microorganisms and vibrates the powdered microorganisms so as to disperse the microorganisms in the internal space 14. The microorganism supply device 130 may be configured so as to disperse the microorganisms by the flow of air generated by a stirring device 28.

An intake valve 36 is connected to an intake port 16 of the processing container 12. By opening the intake valve 36, clean air having passed through an intake filter 38 is introduced into the internal space 14 of the processing container 12. The microorganism supply device 130 disperses the microorganisms in the air introduced into the internal space 14 such that the air in the internal space 14 contains microorganisms of a predetermined concentration. The stirring device 28 stirs the air in the internal space 14 such that the microorganisms float in the air in the internal space 14.

According to the present exemplary variation, since the microorganism supply device 130 is provided in the internal space 14, the concentration of the microorganisms in the internal space 14 can be easily controlled as compared with a case where microorganisms are introduced from the outside of the processing container 12. Thereby, the accuracy of measuring the amount of microorganisms can be improved, and the inactivation performance can be evaluated more suitably.

The present invention has been described based on the embodiment. The invention is not limited to the above-mentioned embodiment, and various design modifications may be added. It will be obvious to those skilled in the art that such modifications are also within the scope of the present invention.

In the above embodiment, a case where microorganisms are inactivated by using ultraviolet rays has been described. In an exemplary variation, radioactive rays such as X rays or γ rays may be used. Further, the above-described technique may be applied to evaluation when microorganisms are inactivated by ion particles, ozone ($O_3$), radical molecules, or the like.

It should be understood that the invention is not limited to the above-described embodiment, but may be modified into various forms on the basis of the spirit of the invention. Additionally, the modifications are included in the scope of the invention.

What is claimed is:

1. An evaluation method comprising:

floating microorganisms with a predetermined concentration in the air inside a processing container having an intake port and an exhaust port;

irradiating the microorganisms floating in the air inside the processing container with ultraviolet rays while the intake port and the exhaust port are closed and while stirring the air inside the processing container;

discharging air that has a volume larger than an inside capacity of the processing container through the exhaust port while introducing air that does not contain microorganisms to be evaluated into the inside of the processing container through the intake port after the irradiation with the ultraviolet rays so as to recover the microorganisms contained in the air that is discharged;

measuring an amount of the microorganisms that have been recovered; and evaluating an inactivation amount of the microorganisms with respect to a spatial average integrated illuminance of the ultraviolet rays inside the processing container in the irradiating.

2. The evaluation method according to claim 1, wherein, in the floating of the microorganisms, air that has a volume larger than the capacity of the inside of the processing container and that contains the microorganisms is introduced through the intake port while discharging the air inside the processing container through the exhaust port.

3. The evaluation method according to claim 1, wherein, in the floating of the microorganisms, microorganisms put inside the processing container are dispersed in the air inside the processing container.

4. The evaluation method according to claim 1, wherein the spatial average integrated illuminance of the ultraviolet rays is calculated by multiplying average illuminance, which is an average value of respective illuminances of the ultraviolet rays on a plurality of virtual planes set inside the processing container, by irradiation time of the ultraviolet rays.

5. The evaluation method according to claim 4, wherein the plurality of virtual planes are set so as to be orthogonal to a predetermined irradiation direction of the ultraviolet rays.

* * * * *